United States Patent [19]

Toida et al.

[11] Patent Number: 4,532,400
[45] Date of Patent: Jul. 30, 1985

[54] LASER IRRADIATING APPARATUS

[75] Inventors: Masahiro Toida, Kanagawa; Norihiro Suenaga, Tokyo; Nobuyuki Suenaga, Kanagawa, all of Japan

[73] Assignee: Nippon Infrared Industries Co., Ltd., Tokyo, Japan

[21] Appl. No.: 445,185

[22] Filed: Nov. 29, 1982

[30] Foreign Application Priority Data

Oct. 1, 1982 [JP] Japan .................................. 57-172984
Nov. 6, 1982 [JP] Japan .................................. 57-194877

[51] Int. Cl.³ ............................................... B23K 26/00
[52] U.S. Cl. .......................... 219/121 LS; 128/303.1; 219/121 LV; 219/121 LQ; 350/96.1
[58] Field of Search ............................ 350/96.1, 96.26; 128/303.1, 4, 6, 395; 219/121 LS, 121 LP, 129/121 LQ, 121 LR, 121 LV, 121 LN, 121 LG

[56] References Cited

U.S. PATENT DOCUMENTS 3,843,865 10/1974 Nath .................................. 128/395 X
4,313,093 1/1982 Suenaga et al. .............. 128/303.1 X
4,408,602 10/1983 Nakajima .......................... 128/303.1

Primary Examiner—C. L. Albritton
Attorney, Agent, or Firm—Cushman, Darby & Cushman

[57] ABSTRACT

A laser irradiating apparatus comprising:
a plurality of laser sources for outputting a plurality of laser beams each having a different wave-length;
a guide beam source for outputting a visible guide beam;
mixing means for coaxially mixing one or more of the laser beams with said visible guide beam;
light guide means for guiding said mixed laser beam and visible guide beam to a desired target;
said laser sources, said guide beam source, said light guide means and said mixing means all being fixed on a single support stand having a support plate;
one or more of said laser sources and said guide beam source being fixed to the same surface of the support plate so as to assure that all irradiated beams from the sources are directed in the same direction and their optical axis are kept in the same distance from the support plate and in parallel thereto.

15 Claims, 4 Drawing Figures

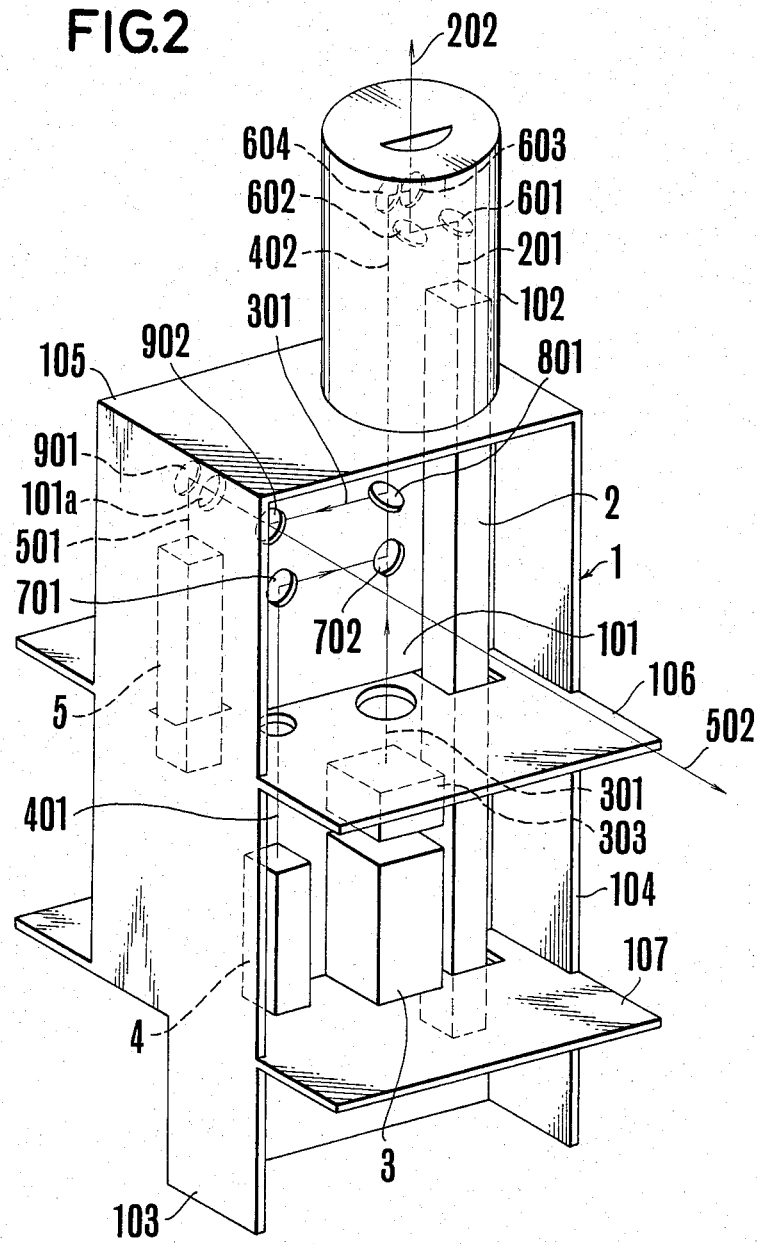

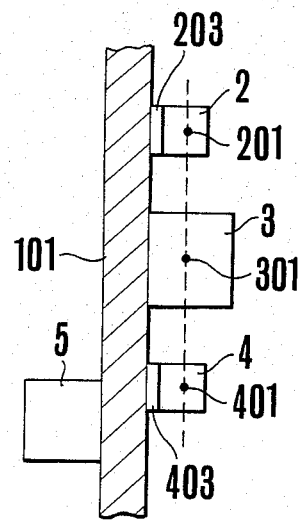
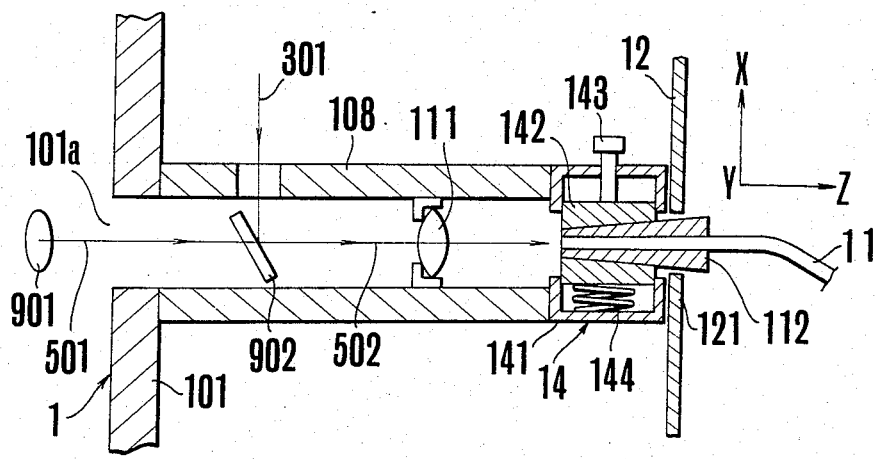

LASER IRRADIATING APPARATUS

BACKGROUND OF THE INVENTION

1. Field of the Invention

This invention relates to a laser irradiating apparatus, and more particularly to a laser irradiating apparatus which is applicable to medical treatments under a most desirable condition. In other words, the present invention relates to an optical system of the laser irradiating apparatus which irradiates simultaneously with a plurality of working laser beams each of which has a different wave-length from others.

2. Description of the Prior Art

It is known that the interaction between a living organism and a laser beam irradiated on the organism varies according to the wave-length of the irradiated laser beam. Simultaneous irradiation of a plurality of laser beams having different wave-lengths to an affected part of the living organism enables to obtain a far better result than the case in which a single laser beam is irradiated.

For example, a combined irradiation of a YAG laser beam which has effectiveness for haemostasis and coagulation and a $CO_2$ laser beam which is excellent for a surgical operation effectively reduces the blooding during the operation. It is known that Ar laser also has an identical effectiveness as the YAG laser.

Apparatus for simultaneous and/or optional irradiation of a plurality of working laser beams having different wave-lengths have been proposed. For example, the Japanese Patent Application Laid-Open No. 130145/81 discloses an apparatus which uses the $CO_2$ laser and the YAG laser and includes two light guides.

In the apparatus of the just above-mentioned prior art, one of the light guides is an articulated arm light guide which simultaneously and/or selectively guides the $CO_2$ laser beam and the YAG laser beam. The other light guide is a fiber light guide which leads only the YAG laser beam. The said light guide is used with an endoscope.

It is noted that the prior art discloses only outline of such apparatus but does not disclose practical and specific disposition relating to a plurality of the working laser sources, guide beam sources and various optical means which are necessary to form an operative and desirable laser irradiating apparatus. It is understood that the laser irradiating apparatus of this type which includes a plurality of working laser sources and irradiates a desired beam together with a visible guide beam, requires various type of optical means and, consequently, the construction of the apparatus is complicated. Therefore, it is indispensable requisite to provide a reasonable disposition or arrangement of the optical means to realize an apparatus which is operative and more effective in practice.

SUMMARY OF THE INVENTION

The present invention has been made to satisfy the requirements mentioned above.

It is an object of the present invention to provide a laser irradiating apparatus equipped with a plurality of working laser beam sources, one or more guide light sources and one or more light guides, in which the layout of these various optical means as hereafter described is rationalized, the optical adjustment is facilitated and the optical stability is excellent.

BRIEF DESCRIPTION OF THE DRAWINGS

FIG. 2 is an illustrative view of a support stand 1 which has been shown in FIG. 1.

FIG. 3 is an illustrative view of the disposition relation of the beams which are irradiated from various type of sources secured to the support stand 1.

FIG. 4 is an illustrative view of a condition in which a fiber light guide 11 and the support stand 1 are connected to each other.

DESCRIPTION OF THE PREFERRED EMBODIMENT

Figure 1:
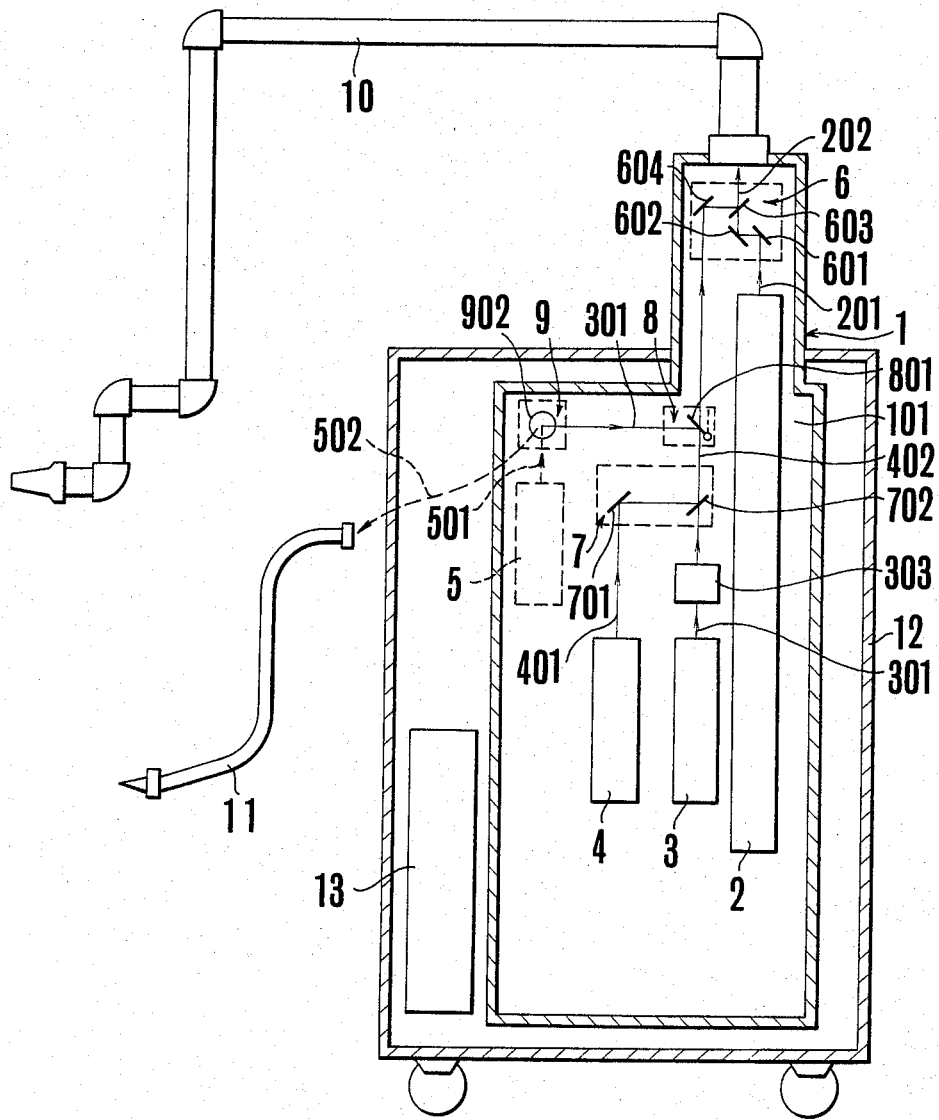
FIG. 1 is an illustrative view of one embodiment of the present invention.

The present invention will be described with reference to the appended drawings.

In FIG. 1, there is shown an apparatus which includes two types of the working laser source, two types of guide beam source and two light guides.

As shown in the drawings, the support stand 1 is installed perpendicularly in the housing 12 in such a manner that a part of it protrudes from the top plate of the housing. Further, there is provided a power source 13 within the housing 12 to supply the power to the laser sources.

On the front surface of a support plate 101, the first working laser source 2 and the second working laser source 3 which provides invisible laser beams, and the first guide beam source 4 which outputs the guide beam, are fixed. On the reverse side of the support plate 101, the second guide beam source 5 which outputs another guide beam is fixed. It is to be noted that all the sources are directed perpendicularly and upwardly so that the output beams are directed perpendicularly and upwardly.

As the first working laser source 2, such a source which has high ability for incision, for example, a $CO_2$ laser is used to output the first laser beam 201. As the second working laser source 3, such a source which has a high ability for coagulation of blood, for example, a YAG laser source is used to output the second laser beam 301. Further, as a first guide beam source 4, a He-Ne laser source is used to output the first guide beam 401 which is red. As the second guide beam source 5, a halogen lamp is used to output the guide beam 501 which is white.

On the front surface of the support plate 101, a second mixing means 7 is fixed to coaxially mix the second laser beam 301 and the first guide beam 401. The mixing means 7 consists of a reflecting mirror 701 which reflects the first guide beam 401, and a dichroic mirror 702 which allows the second laser beam 301 to pass through but reflects the first guide beam 401. Each of the mirrors 701 and 702 is fixedly mounted through a mirror holder (not shown) to the support plate 101. In the mixing means 7, the above-mentioned two laser beams are coaxially mixed to output the beam 402.

In this particular case, the laser beam 301 which is input to the second mixing means 7 is collimated by a conventional correction optical means 303. The reason for it is that when the second laser source is the YAG laser, particularly when it is a multi-mode oscillation YAG laser, a beam divergence approach 14-15 mrad and the diameter of the beam becomes excessively large. Consequently, it becomes difficult to use an articulated arm light guide. In place of the correction optical means 303 an output mirror which has a curvature may be used as the second working laser source 3 to correct the beam divergence. The correction optical means 303 is also fixed to the support plate 101.

In an identical manner, a first mixing means 6 is fixed to the front surface of the support plate 101 to coaxially mix the first laser beam 201 and the said beam 402. The mixing means 6 consists of reflecting mirrors 601 and 602 which reflect the first laser beam 201, another reflecting mirror 604 which reflects the said beam 402, and a dichroic mirror 603 which allows the first laser beam 201 but reflects the said beam 402. Each of the mirrors 601 through 604 is fixed through a mirror holder (not shown) to the support plate 101. The two beams which are coaxially adjusted by the mixing means 6, are output as a beam 202 as shown in the drawing.

As clearly shown, the first mixing means 6 is so designed that the beam 402 reflected by the reflecting mirror 604 and the first laser beam 201 reflected by the reflecting mirrors 601 and 602 are coaxially mixed by the dichroic mirror 603. Thus, the beam 402 is reflected only twice for the mixing so that the loss of the second laser beam 301 during the transmission can be advantageously saved.

The position and angle of the beam 402 are adjusted by the reflecting mirror 604 and the dichroic mirror 603, while the position and angle of the first laser beam 201 are adjusted by the reflecting mirrors 601 and 602.

The beam 202 is introduced to an articulated arm light guide which is mounted in a conventional manner to the top of the support stand 1 and, irradiated to a required part. The light guide 10 is used for surgical operation. An axis of the beam 202 is adjusted to coincide with the axis of the light guide 10 by adjusting the mirrors disposed within the first mixing means 6.

An optical path change-over means 8 is disposed to the support plate 101. The means 8 changes over the optical path of the beam 402 by displacing the reflection mirror 801 which is fixed to a rotary solenoid (not shown) into the beam 402. The arrangement is such that when the reflection mirror 801 is moved to a withdrawn position, the beam 402 advances directly into the first mixing means 6. When the reflection mirror 801 is in an advanced position, the optical path of the beam 402 is changed over. In changing over the optical path, irradiation from the first guide beam source 4 is suppressed by suitable means and the second laser beam 301 is irradiated into the third mixing means 9 which will be described hereinafter.

On the reverse side of the support plate 101, a reflection mirror 901 (refer to FIG. 2) which reflects the second guide beam 501, is fixed. On the front surface of the support plate 101, a dichroic mirror 902 which reflects the second laser beam 301 and allows the second guide beam 501, is fixed. The mirrors 901 and 902 are fixed to the support plate 101 through the mirror holders (not shown). A third mixing means 9 consists of the two mirrors 901 and 902.

The second guide beam 501 is reflected by the reflection mirror 901 and directed so that the guide laser beam 502 passes through an opening 101a (refer to FIG. 2) which is formed in the support plate 101 and introduced to the dichroic mirror 902. The second laser beam 301 is also introduced to the mirror 902 and coaxially mixed with the second guide beam 501. Both beams adjusted coaxially are output as a beam 502 as shown in the drawing.

The beam 502 is directed so that the beam 502 is introduced to a fiber light guide 11 which is connected to the support stand 1 by a complying means described hereinafter. Consequently, the beam 502 can be irradiated through the fiber light guide 11 to a required part. The fiber light guide 11 is incorporated in an endoscope apparatus to apply it to surgical operations under an endoscope visual field.

It is understood that the apparatus of the embodiment is operated in one of irradiation modes which are described hereinbelow.

(1) In the first mode the operation of the optical path change-over means 8 is displaced to a withdrawn position, and the first working laser source 2 and the second working laser source 3 are driven. The first laser beam 201, the second laser beam 301, and the first guide beam 401 are coaxially irradiated through the articulated arm light guide 10.

(2) In the second mode the optical path change-over means 8 is displaced to a withdrawn position and only the first working laser source 2 is driven. The first laser beam 201 and the first guide beam 401 are coaxially irradiated through the articulated arm light guide 10.

(3) In the third mode the optical path change-over means 8 is displaced to a withdrawn position and only the second working laser source 3 is driven. The second laser beam 301 and the first guide beam 401 are coaxially irradiated through the articulated arm light guide 10.

4) In the fourth mode the optical path change-over means 8 is displaced to an advanced position and only the second working laser source 3 is driven. The second laser beam 301 and the second guide beam 501 are coaxially irradiated through the fiber light guide 11.

Further, in this embodiment, the optic axis alignment at each incident end of the articulated arm light guide 10 and fiber light guide 11 can be performed in the following procedure:

For the optic axis alignment for the articulated arm light guide 10, the optical path change-over means 8 is set to the withdrawn position so as to irradiate the first guide beam 401. As hereinbefore described, the first guide beam, 401 is reflected and directed to the light guide 10. The first guide beam 401 is coaxially adjusted both with the first laser beam 201 and the second laser beam 301. The alignment may be performed in such a manner that, while visually observing the first guide beam 401, the beam is adjusted to coincide with the center portion (optic axis of the articulated arm light guide) of the end of the light guide 10.

On the other hand, for the optic axis alignment of the fiber light guide 11, the optical path change-over means 8 is set to the advanced position and the first guide beam source 4 is driven. The first guide beam 401 output from the first guide beam source 4 is propagated along the same optical path as the second laser beam 301 and directed to the fiber light guide 11.

Thus, the alignment may be performed in such a manner that while visually observing the first guide beam 401, the position of the light guide 11 is adjusted as hereinafter described so as to introduce the beam into the incident end of the fiber light guide 11.

However, the second guide beam 501 output from the second guide beam source 5 is not coherent light and the beam cannot be minutely diaphragmed. So, it cannot be a marker for positioning of the fiber light guide 11.

In addition, according to the present invention, the second laser beam 301 and the first guide beam 401 are mixed after both have been once output from their sources 3 and 4. Accordingly, there is no possibility that the beam divergence of the first guide beam is disturbed by the correction optical means 303. Also, as this is not the conventional type in which the first guide beam is induced into the totally reflecting mirror side of the second working laser source 3, there is no possibility that the heated lens effect for a YAG laser rod will cause the first guide beam 401 to wave. Therefore, the articulated arm light guide can be used as a convenient light guide.

An arrangement relating to the various optical means is given referring to FIGS. 2 through 4 hereinafter.

FIG. 2 is illustrative of the support stand which has been shown in FIG. 1. The support stand 1 is integrally formed by casting. The support plate 101 within the support stand 1 is formed from a sheet of plate and has a protruded part. As above-mentioned, the protruded part of the support plate 101 protrudes outwardly from the top plate of the housing. It is noted that the part of the support plate 101 lower than its shoulder is housed within the housing. There are provided side plates 103, 104 and 105 to surround the support plate 101. The side plates further serves to prevent twisting and bending of the support plate 101. On the side plate 105, a cylindrical body 102 is disposed to surround the protruded part of the support plate 101. In the drawing, numerals 106 and 107 stand for reinforcing plates for the support stand 1. Two openings are provided in the reinforcing plate 106 for the second laser beam 301 and the first guide laser beam 401 to pass through.

As above-mentioned, the first working laser source 2, the second working laser source 3, the first guide beam source 4 and the second guide beam source 5 are disposed vertically upwardly on the support plate 101 of the support stand 1. It is important here that all the beams irradiated from these sources should be directed in the same direction. As the second guide light source 5 is not disposed on the front surface of the support plate 101, it is not always necessary to dispose it in the same direction as other beam sources. Such a layout causes each beam irradiated from each source to be kept in parallel to one another. Therefore, the second working laser beam 301 and the first guide beam 401 may be kept in parallel relation while being introduced into the second mixing means 7. Into the first mixing means 6, the first working laser beam 201 and beam 402, in parallel relation each are introduced.

The first working laser source 2, the second working laser source 3, and the first guide beam source 4 are disposed on the support plate 101 in such a manner that axis of the irradiated beams 201, 301 and 401 of the sources 2, 3 and 4 are at equal distance from the surface of the support plate 101 and run parallel with it as illustrated in FIG. 3. Accordingly, when the second working laser beam 301 and the first guide beam 401 are introduced into the second mixing means 7, the optical axis of each beam is kept parallel relation and at the same distance from the support plate 101. As the beam 402 is coaxial to the second working laser beam 301, when the beam 402 and the first working laser beam 201 are introduced into the first mixing means 6, the optical axis of each beam is kept in parallel relation, and at the same distance from the support plate 101. Therefore, mixing operations of said beams are performed on a plane which is kept in parallel with the support plate 101. The distance from the surface of the support plate 101 to each of the axis of each beams can be adjusted, for example, by means of the spacers 203 and 403.

As illustrated in FIG. 4, a cylindrical body 108 (not shown in FIG. 2) is mounted in a manner to surround an opening 101a which is provided in the support plate 101. An adjusting mechanism 14 is provided at the top end of the cylindrical body 108 and is directed to the other opening 121 which is provided in the housing 12. A connector 112 which is provided at the base end of the fiber light guide 11 detachably connected to the adjusting mechanism 14 through the opening 121. Then, the beam 502 which is obtained by mixing of the second working laser beam 301 and the second guide beam 501 is introduced to the fiber light guide 11. Numeral 111 in the drawing shows a condenser to condense the beam 502.

Accordingly, summarizing the foregoing, in this invented apparatus, all the optical means such as the first and second working laser sources 2 and 3, the first and second guide beam sources 4 and 5, the first to third mixing means 6, 7 and 9, the optical path change-over means 8 and the first and second light guides 10 and 11 are installed on the support stand 1.

The incident end of the fiber light guide 11 is adjusted in a plane which extends perpendicularly to an axial direction of the beam 502. The adjusting mechanism 14 is arranged such that a slider 142 is located within the housing 141, and one side of the slider 142 is compressed by a spring 144 and the other side is contacted with a screw 143. It is understood that the slider 142 is made displaceable along an axis X as illustrated in the drawing by loosening the screw 143. Further, there are provided another screw and another spring in a position at a right angle to the spring 144 and the screw 143 (both of them are not shown). The slider 142 is made displaceable along the axis Y by loosening another screw. With the arrangement, the incident end of the fiber light guide 11 can easily be aligned to the axis of the beam 502.

As described hereinbefore, the second working laser beam 301 and the first guide beam 401 are mixed prior to the mixing of the first working laser beam 201 and the second working laser beam 301. Accordingly, visible guide beam 401 can be used as a marker for the alignment for the fiber light guide 11 and the articulated arm light guide 10.

In the above described embodiment, the second guide beam source 5 can be omitted. In this case, however, the third mixing means 9 is also omitted, and the first guide beam 401 is irradiated independently of the position of the said means 8. In this case, instead of the third mixing means a reflecting mirror is required to direct the beam 402 to the fiber light guide 11. Further, it is noted that all of the beam sources and the mixing means are not required to be disposed on the support plate 101. Some of them may be disposed on the side plates which have previously been described. In this case, however, each axis of the irridiated beams of the sources must have an equal distance from the surface of the support plate 101. Further in the embodiment, the fiber light guide 11 can be omitted. In this case however, the optical path change-over means 8, the second guide beam source 5, and the third mixing means 9 are also omitted.

As previously described, the laser irradiating apparatus of the present invention has such features as mentioned below.

(1) All the optical means such as the working laser sources, the guide beam sources, the mixing means, the optical path change-over means, and the light guides are mounted to the single support stand.

(2) The working laser sources and the guide beam sources on the front surface of the support plate of the support stand are disposed in such a manner that all the beams irradiated from the sources are directed in the same direction. Further, each of the sources is disposed on the front surface of the support plate in such a manner that the axis of the beam which has been irradiated from each source has an equal distance from the support plate and is kept parallel thereto.

(3) The first guide beam which is output from the first guide beam source (a visible laser source) is mixed with the second laser beam before it is introduced into the optical path change-over means.

(4) The second laser beam which is output from the second laser source is coaxially mixed with the first guide beam which is output from the first guide beam source after these beams are projected from their respective beam sources.

The laser irradiating apparatus according to the present invention is arranged such that when it has received any vibration or impact and the position of the support stand has been changed, the optical system of the apparatus does not present any abnormality. Because almost every means including beam generating means, beam transmission means, and other optical means are disposed on the single support stand.

In case the support stand has had some stretches and/or shrinkage due to the heat or aging the optical means disposed on the single support stand receive almost equal amount of change. In other words, even when some changes have taken place in the positional relation of the optical means, still the relative displacement of each of the means is rather small. Therefore, the present invention provide an apparatus which has high stability regarding the optical paths. Desirably, the support stand is integrally formed (for example, casting etc.). Alternately, the support stand is disposed within the housing in a manner that the support stand is suspended by some damping means to decrease the effect of the vibration and/or impact.

Also, according to the present invention, all the beams irradiated from the beam sources installed on the front surface of the support plate of the support stand are directed in the same direction and kept parallel to one another. In addition, these beams are located at the same distance from, and kept in parallel with the support plate. Accordingly, two beams kept in parallel relations and at the same distance from the support plate are introduced in each mixing means. Therefore, the above-mentioned arrangement facilitates mixing of each beam. The arrangement is such that the number of mirrors which are required in mixing of the beams can be decreased.

The above-mentioned advantage is indispensable to the apparatus which includes a plurality of laser sources and the optical system which is complicated in its structure to simplify and stabilize the optical system.

Further, according to the present invention, as described in connection with the third feature, the structure is so designed that the first guide beam and the second working laser beam initially mixed together so that the first guide beam can be used as a marker for the optical axis alignment of the incident ends of the two light guides. Therefore, it is possible to easily perform the optical axis alignment of individual light guides and the labour required for the optical adjustment can be reduced.

Although detailed description is omitted, the first working laser beam and the first guide beam are initially mixed together. A complicated optical system must be incorporated for performing the optical axis alignment of the individual light guides mentioned above.

Further as described in connection with the fourth feature of the present invention, the mixing of the second laser beam and the first guide beam is performed after they have been projected from the beam sources. This is particularly advantageous where the articulated arm light guide is used as the light guide as mentioned hereinbefore.

The third feature produces peculiar effects irrespective of the first and second features, and can be advantageously incorporated in an apparatus equipped with two light guides.

What we claim:

1. A laser irradiating apparatus comprising:
   a plurality of laser sources for outputting a plurality of laser beams each having a different wave-length;
   a guide beam source for outputting a visible guide beam;
   mixing means for coaxially mixing at least one of the laser beams with said visible guide beam;
   light guide means for guiding said mixed laser beam and visible guide beam to a desired target;
   said laser sources, said guide beam source, said light guide means and said mixing means all being fixed on a single support stand having a support plate; and
   at least one of said laser sources and said guide beam source being fixed to the same surface of the support plate so as to assure that all irradiated beams from the sources are directed in the same direction and their optical axis are kept at the same distance from the support plate and in parallel thereto.

2. A laser irradiating apparatus according to claim 1, which further comprises another light guide means and optical path change-over means for changing over at least one of the laser beams to direct beam to the another light guide means, said another light guide means and the optical path change-over means being fixed on the support stand.

3. A laser irradiating apparatus according to claim 2, which further comprises another guide beam source on a reverse side of the support plate and another mixing means for coaxially mixing a visible guide beam from the another guide beam source with the laser beam directed by the optical path change-over means to the another light guide means, said another mixing means being fixed on the support stand.

4. A laser irradiating apparatus according to claim 1, in which the laser source and the guide beam source are supported on the support plate with a spacer inserted therebetween so as to keep the distances from the axis of the irradiated beam of each source to the support plate equal to each other.

5. A laser irradiating apparatus according to claim 1, in which the laser sources comprises a first laser source for outputting a first laser beam effective mainly for incision of an object and a second laser source for outputting a second laser beam effective mainly for coagulation of the object, and the light guide means is a first light guide mainly for surgical operation and the another light guide means is the second light guide mainly for use in an endoscope device.

6. A laser irradiating apparatus according to claim 1, wherein said support stand support plate has a protruded portion, and said support stand is perpendicularly disposed within a housing so that said working laser sources and said guide beam source are directed upwardly and vertically.

7. A laser irradiating apparatus according to claim 6, which further comprises side plates attached to ends of the support plate, reinforcing plates which are disposed perpendicularly to the said support plate, and a cylindrical body which is disposed in a manner to surround the said protruded portion, whereby said first light guide is disposed on the top end of the cylindrical body.

8. A laser irradiating apparatus according to claim 7, wherein the said support stand is integrally formed by casting.

9. A laser irradiating apparatus according to claim 4, wherein the said second light guide is a fiber light guide, which is disposed on a cylindrical body disposed on the support plate.

10. A laser irradiating apparatus according to claim 5, wherein the other guide beam source is a halogen lamp.

11. A laser irradiating apparatus comprising:
a first laser source for outputting a first laser beam;
a second laser source for outputting a second laser beam;
a first mixing means for coaxially mixing the first laser beam with the second laser beam;
a first light guide for guiding at least one of the first laser beam and the second laser beam from the first mixing means to a desired target;
optical path change-over means for changing over the optical path of the second laser beam;
a second light guide for guiding the second laser beam changed over in the optical path by the change-over means to a desired target; and
a guide beam source for outputting a laser beam used as a visible guide beam, said second laser beam and the guide beam being coaxially mixed by the second mixing means prior to introduction to the optical path change-over means.

12. A laser irradiating apparatus according to claim 11, in which the first laser source is a $CO_2$ laser, the second laser source is a YAG laser, and the guide beam source is a He-Ne laser.

13. A laser irradiating apparatus according to claim 11, in which the first light guide is an articulated arm light guide, and the guide beam and the second laser beam are coaxially mixed by a dichroic mirror and a reflecting mirror after projection from their sources.

14. A laser irradiating apparatus according to claim 13, which further comprises correction optical means for collimating the second laser beam.

15. A laser irradiating apparatus according to claim 11, in which the first mixing means comprises two reflecting mirrors for reflecting the first laser beam, another reflecting mirror for reflecting the second laser beam and the guide beam, and a dichroic mirror for reflecting the second laser beam and the guide beam but penetrating the first laser beam.

* * * * *